(12) United States Patent
Wagner et al.

(10) Patent No.: US 10,550,047 B2
(45) Date of Patent: *Feb. 4, 2020

(54) PROCESS FOR THE PRODUCTION OF OLIGOMERIZED OLEFINS

(71) Applicant: BASF SE, Ludwigshafen (DE)

(72) Inventors: Hans-Guenter Wagner, Neuleiningen (DE); Christoph Bayer, Nuremberg (DE); Lothar Karrer, Pfungstadt (DE); Sven Crone, Limburgerhof (DE); Markus Eggersmann, Speyer (DE); Kam Wing Wong, Tsuen Wan (CN); Patrik Pietz, Shanghai (CN); Heinz Ruetter, Xanten (DE)

(73) Assignee: BASF SE, Ludwigshafen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/517,695

(22) PCT Filed: Oct. 9, 2014

(86) PCT No.: PCT/CN2014/088231
§ 371 (c)(1),
(2) Date: Apr. 7, 2017

(87) PCT Pub. No.: WO2016/054788
PCT Pub. Date: Apr. 14, 2016

(65) Prior Publication Data
US 2017/0247298 A1    Aug. 31, 2017

(51) Int. Cl.
*C07C 2/10*    (2006.01)
*C07C 5/03*    (2006.01)
*C07C 5/05*    (2006.01)

(52) U.S. Cl.
CPC .......... *C07C 2/10* (2013.01); *C07C 5/03* (2013.01); *C07C 5/05* (2013.01); *C07C 2521/04* (2013.01);
(Continued)

(58) Field of Classification Search
CPC .......... B01D 15/00; B01D 2259/40086; B01D 3/141; C07C 2/06; C07C 5/03;
(Continued)

(56) References Cited

U.S. PATENT DOCUMENTS 3,208,157 A    9/1965    Stark
3,725,377 A    4/1973    Cottle
(Continued)

FOREIGN PATENT DOCUMENTS

DE    198 45 857 A1    4/2000
DE    10 2008 007 081 A1    8/2009
(Continued)

OTHER PUBLICATIONS

International Search Report dated Jul. 8, 2015 in PCT/CN2014/088231.
(Continued)

*Primary Examiner* — Sharon Pregler
(74) *Attorney, Agent, or Firm* — Oblon, McClelland, Maier & Neustadt, L.L.P.

(57) ABSTRACT

A process for the production of oligomerized olefins comprising the following steps: purification of an organic composition (OC1) in at least one adsorber to obtain an organic composition (OC2); oligomerization of organic composition (OC2) in the presence of a catalyst to obtain an organic composition (OC3); distillation of organic composition (OC3) in a distillation column (D1) to obtain an organic composition (OC4) from the upper part of (D1) and an organic composition (OC5) from the lower part of (D1);
(Continued)

hydrogenation of organic composition (OC4) to obtain an organic composition (OC11) and regeneration of an adsorber (A1) employing organic composition (OC11) as regeneration media.

17 Claims, 2 Drawing Sheets

(52) U.S. Cl.
CPC ...... *C07C 2521/06* (2013.01); *C07C 2521/08* (2013.01); *C07C 2523/04* (2013.01); *C07C 2523/755* (2013.01)

(58) Field of Classification Search
CPC ......... C07C 11/02; C07C 67/303; C07C 6/04; C07C 7/08; B01J 2231/645; B01J 23/755; B01J 31/0212; B01J 31/122
USPC ....... 585/255, 820, 826, 502, 500, 512, 258, 585/250
See application file for complete search history.

(56) References Cited

U.S. PATENT DOCUMENTS

| | | | |
|---|---|---|---|
| 4,814,517 A * | 3/1989 | Trubac | C07C 41/36 568/697 |
| 5,288,370 A * | 2/1994 | Asselineau | C07C 7/08 203/51 |
| 6,271,430 B2 * | 8/2001 | Schwab | B01D 3/141 585/313 |
| 6,281,397 B1 * | 8/2001 | Santi | B01J 31/0212 585/250 |
| 7,803,332 B2 | 9/2010 | Brown et al. | |
| 8,779,228 B2 | 7/2014 | Heidemann et al. | |
| 2006/0122446 A1 | 6/2006 | Louret et al. | |
| 2006/0270882 A1 | 11/2006 | Brown et al. | |
| 2007/0123743 A1 | 5/2007 | Ng et al. | |
| 2009/0023882 A1 | 1/2009 | Hanefeld et al. | |
| 2010/0056834 A1 | 3/2010 | Phillion et al. | |
| 2011/0301398 A1 * | 12/2011 | Heidemann | C07C 2/10 585/512 |
| 2013/0131416 A1 * | 5/2013 | Crone | C07C 2/06 585/329 |

FOREIGN PATENT DOCUMENTS

| | | |
|---|---|---|
| DE | 10 2012 212 316 A1 | 1/2014 |
| EP | 1 724 249 A2 | 11/2006 |
| WO | WO 00/59849 A2 | 10/2000 |
| WO | WO 01/83407 A1 | 11/2001 |
| WO | WO 2005/005877 A1 | 1/2005 |
| WO | WO 2005/056503 A1 | 6/2005 |
| WO | WO 2006/130192 A1 | 12/2006 |
| WO | WO 2010/024958 A2 | 3/2010 |
| WO | WO 2010/057905 A1 | 5/2010 |
| WO | WO 2016/054785 A1 | 4/2016 |
| WO | WO 2016/054786 A1 | 4/2016 |
| WO | WO 2016/054787 A1 | 4/2016 |
| WO | WO 2016/054788 A1 | 4/2016 |
| WO | WO 2016/054789 A1 | 4/2016 |
| WO | WO 2016/054790 A1 | 4/2016 |

OTHER PUBLICATIONS

International Preliminary Report on Patentability and Written Opinion dated Apr. 11, 2017 in PCT/CN2014/088231.
Search Report dated Jun. 4, 2018 in European Patent Application No. 14903583.4, 3 pages.

* cited by examiner

PROCESS FOR THE PRODUCTION OF OLIGOMERIZED OLEFINS

The invention relates to a process for the production of oligomerized olefins. For the reduction of the amount of compounds containing oxygen and/or sulphur, an organic composition (OC1) comprising at least one alkane, at least one olefin and at least one compound containing oxygen and/or sulphur is fed into at least one adsorber, yielding an organic composition (OC2) comprising at least one alkane, at least one olefin and a reduced amount of at least one compound containing oxygen and/or sulphur compared to the respective amount in organic composition (OC1).

The organic composition (OC2) is subjected to a catalyzed oligomerization wherein at least one of the olefins is at least partially oligomerized, obtaining an organic composition (OC3) comprising a reduced amount of at least one olefin and an increased amount of at least one oligomerized olefin, compared to the respective amounts in (OC2).

Organic composition (OC3) is fractionated in a distillation column (D1), wherein an organic composition (OC4) is obtained from the upper part of (D1) and (OC4) comprises at least one alkane, at least one olefin and a reduced amount of at least one oligomerized olefin compared to the respective amount in (OC3). From the lower part of (D1) an organic composition (OC5) is obtained comprising at least 80% by weight, preferably at least 95% by weight of the at least one oligomerized olefin present in organic composition (OC3).

Organic composition (OC4) is hydrogenated in order to obtain an organic composition (OC11) comprising at least one alkane and a further reduced amount of the at least one olefin and/or the at least one oligomerized olefin compared to organic composition (OC4). Organic composition (OC11) is employed as regeneration media for regeneration of an adsorber.

Higher olefins, like octenes and dodecenes are of interest as starting materials for further functionalization such as hydroformylation and subsequent hydrogenation into alcohols or as components of fuels such as gasoline, diesel or kerosene.

Other processes for the oligomerization of olefins are generally known to the person skilled in the art.

WO 2010/057905 A1 discloses a process for the oligomerization of olefins by bringing at least one C2 to C8 olefin into contact with a nickel containing heterogeneous catalyst. Preferably the olefins are passed over an adsorption material before being brought in contact with the catalyst in order to prevent catalyst poisoning. However, WO 2010/057905 A1 does not disclose the use of an organic composition obtained as by-product for the regeneration of an adsorber for purification of the starting materials.

DE 10 2008 007 081 A1 discloses a process for the production of n-butene-oligomers and 1-butene from a technical mixture-I of $C_4$-hydrocarbons. Analogously to WO 2010/057905 A1, the document mentions the need for the removal of certain compounds containing heteroatoms out of the hydrocarbon mixture intended to be used in the catalyzed oligomerization process. The document does not disclose the reuse of a by-component of the starting material mixture for the oligomerization process in the regeneration of an adsorber for purification of the starting material.

WO 2005/056503 A1 discloses a composite catalyst for the selective oligomerization of lower alkenes and the production of high octane products. While the oligomerization of lower alkenes and mixtures of alkenes is reported in detail, the use of adsorbers for purification of the starting materials for the oligomerization and the use of a by-component of the starting material mixture for the regeneration of these adsorbers is not mentioned.

WO 01/83407 describes a process for the oligomerization of alkenes having from 3 to 6 carbon atoms using a catalyst containing a zeolite of the MFS structure type under conditions to obtain selectively oligomeric product containing predominant amount of certain oligomers. Like in the previously discussed document of prior art neither the use of adsorbers for purification of starting materials mixtures for oligomerization nor their regeneration by use of a by-component of the starting material mixture is part of the disclosure.

WO 00/59849 discloses a method for oligomerization of C2- to C8 olefins on a heterogeneous catalyst containing nickel. The authors do not report the use of by-components of the starting material mixture for regeneration of an adsorber of the process.

WO 2005/05877 A1 describes the application of acids as catalysts in the oligomerization of olefins. A metal catalyzed oligomerization is not disclosed. Further, the application does not deal with the use of by-components of the starting material mixture in the regeneration of an adsorber integrated in the process.

WO 2006/130192 A1 discloses a reactor system comprising at least one reactor wherein makeup water for said system is preheated by water/steam exiting said reactor. In one embodiment the reactor system is employed for the oligomerization of olefins. Analogue to the preceding documents of prior art, the regeneration of an adsorber which is part of the process with a by-component of the starting material mixture is not mentioned.

US 2006/0122446 A1 discloses a reaction device with staged reaction zones making it possible to implement strongly endothermic or exothermic reactions. The device reduces the differences in catalytic activity between these zones using an addition of fresh or regenerated catalyst at the inlet of each reaction zone and provides an integrated heat exchanger. In particular, the device is applied for oligomerizations of olefins. The use of by-components of the starting material mixture for regeneration of an adsorber integrated in the process is not part of the disclosure.

WO 2010/024958 A2 describes an oligomerization process for olefins and a method for isolating linear butenes from a mixed product feed. While the need for removing compounds containing heteroatoms to prevent poisoning of the oligomerization catalyst for certain embodiments of the invention is mentioned, the regeneration of an adsorber serving this purpose, incorporated in the process, by by-components of the starting material mixture is not disclosed.

The processes for oligomerization of olefins disclosed in prior art mainly focus on the oligomerization and/or isolation of the products and do, in most cases, not mention concrete steps concerning purification of starting materials and their integration in the overall process. However, in order to create an overall efficient process with high throughput and low energy and material cost, the efficient integration of adsorbers for purification of starting material mixtures as well as isolation steps is likewise of high interest, opening possibilities for advantageous synergy effects.

The problem underlying the present invention consists in the development of a new process for the production of oligomerized olefins.

The object is achieved by a process for the production of oligomerized olefins comprising the following steps a) to e):
a) purification of an organic composition (OC1) comprising at least one alkane, at least one olefin and at least one compound containing oxygen and/or sulphur wherein (OC1) is fed into at least one adsorber in order to obtain an organic composition (OC2) comprising at least one alkane, at least one olefin and a reduced amount of at least one compound containing oxygen and/or sulphur compared to the respective amount in organic composition (OC1), b) oligomerization of organic composition (OC2) in the presence of a catalyst, wherein at least one of the olefins of (OC2) is at least partially oligomerized, obtaining an organic composition (OC3) comprising a reduced amount of at least one olefin and an increased amount of at least one oligomerized olefin, compared to the respective amounts in (OC2);

c) distillation of organic composition (OC3) in a distillation column (D1), wherein
   i) an organic composition (OC4) is obtained from the upper part of (D1) and (OC4) comprises at least one alkane, at least one olefin and a reduced amount of at least one oligomerized olefin compared to the respective amount in (OC3),
   ii) an organic composition (OC5) is obtained from the lower part of (D1) and (OC5) comprises at least 80% by weight, preferably at least 95% by weight of the at least one oligomerized olefin present in organic composition (OC3);

d) hydrogenation of organic composition (OC4) to obtain an organic composition (OC11) comprising at least one alkane and a further reduced amount of the at least one olefin and/or of the at least one oligomerized olefin compared to organic composition (OC4), e) regeneration of an adsorber (A1) employing organic composition (OC11) as regeneration media.

The process according to the present invention provides a process for the oligomerization of olefins in which besides the oligomerization step itself, further necessary process steps like purification of starting materials by adsorbers or isolation of products are already integrated in an advantageous manner in the overall process, taking advantage of synergetic effects, increasing overall throughput, lowering energy consumption and overall costs.

A further advantage of the inventive process is the applicability of several embodiments of the inventive process for oligomerization of olefins, including purification and isolation steps on an industrial scale.

Compared to other processes of prior art, no additional purification step to remove compounds containing sulfur and/or oxygen or other heteroatoms from the regeneration media is required since these hydrocarbon mixtures are obtained for example as by-products during purification of the starting material mixture comprising olefins by means of adsorbers. The purchase of alternative regeneration media like inert gases is therefore avoided.

Another advantage of the present invention can be seen in the fact that the invention allows the operation of at least one adsorber in regeneration mode parallel to the operation of at least one other adsorber in operation mode in the same plant. In combination with the possible application of equal times for regeneration and operation mode, delays in the process or idling times are minimized.

Hydrocarbons comprising residual olefins, corresponding to organic composition (OC11) within the context of the present invention, can be applied for adsorber regeneration, without significant formation of detrimental precipitates of coke and polymers on the adsorbent. Within the context of the present invention, the organic composition (OC11) is being employed as regeneration medium of an adsorber.

Consequently, the efficient purification steps for removing compounds containing heteroatoms allow the use of starting material mixtures with a relatively high content of compounds containing heteroatoms, in particular compounds containing oxygen and/or sulphur.

In summary, operating costs and environmental burden are lowered by reduction of energy consumption, waste, recovery of product and recycling of by-product as regeneration media due to a combination of advantageous measures implemented in the present invention.

The invention is specified in more detail as follows:

The present invention relates to a process for the production of oligomerized olefins comprising the following steps a) to e):

In step a) an organic composition (OC1) comprising at least one alkane, at least one olefin and at least one compound containing oxygen and/or sulphur is purified wherein (OC1) is fed into at least one adsorber in order to obtain an organic composition (OC2) comprising at least one alkane, at least one olefin and a reduced amount of at least one compound containing oxygen and/or sulphur compared to the respective amount in organic composition (OC1).

Preferably the alkane contains 1 to 14, more preferably 3 to 10, most preferably 4 to 6 carbon atoms in its longest chain.

The at least one alkane can be, for example, linear, branched and/or cyclic and is selected from the group: methane, ethane, propane, butane, pentane, hexane, heptane, octane, nonane and decane. Preferably the at least one alkane is butane.

In the context of the present invention, if not stated otherwise, it is not differentiated between the different isomers of a certain alkane. For example, the term butane may refer to n-butane and/or isobutane.

The organic compositions, within this invention, may comprise in a specific embodiment one or more further alkanes different from butane, which may be selected from the same alkanes as specified above.

The alkane in organic composition (OC1) is preferably butane and the olefin in (OC1) is preferably butene.

The at least one olefin may comprise at least one linear, branched, cyclic monoolefin and/or at least one linear, branched, cyclic olefin containing more than one olefinic double bond. Preferably the olefin has 2 to 14, more preferably 3 to 10, most preferably 4 to 6 carbon atoms in its longest carbon chain.

If more than one stereoisomer of an olefin exists, e.g. the corresponding cis- and trans-isomer, these isomers are, in the context of the present invention, regarded as equivalent. Further, it is not differentiated between constitutional isomers of monoolefins. For example, the term butene may comprise the constitutional isomers 1-butene and/or 2-butene as well as 2-butene the corresponding cis- and/or trans-stereoisomer.

Monoolefins can be, for example, selected from the group: ethene, propene, butene pentene, hexene, heptene, octene, nonene and decene. Preferably, the olefin is butene. If at least one olefin containing more than one olefinic double bond is present, this olefin is preferably a diene, more preferably butadiene.

The organic compositions comprising at least one olefin may comprise in a specific embodiment one or more further olefins different from butene which may be selected from the same olefins as specified above.

The organic composition (OC1) may comprise at least 20 wt-% of the at least one olefin, preferably butene and/or at least 20 wt-% of the at least one alkane, preferably butane.

The organic composition (OC1) preferably comprises at most 1 wt-% of compounds containing oxygen and/or sulfur.

The organic composition (OC1) preferably comprises at least 15 wt-ppm of at least one compound containing oxygen and/or sulfur.

The organic composition (OC1) comprises at least one halogen and/or halogen-containing compound.

The organic composition (OC2) preferably comprises not more than 20 wt-ppm of compounds containing oxygen and/or sulphur.

Further, (OC1) may be saturated with water.

The organic composition (OC2) preferably comprises at least 50 wt-ppb of compounds containing oxygen and/or sulfur.

The organic composition (OC2) preferably comprises not more than 0.1 wt-%, more preferably 0 wt-% of at least one oligomerized olefin, preferably the at least one olefin is octene.

Within the context of the present invention, the term "adsorber" comprises the adsorbent as well as the device in which the adsorbent is embedded in. Instead of the term "adsorbent" the expression "adsorber material" may be used. The term adsorber may be used equivalently for adsorbent, even if a certain statement actually refers only to the adsorbent but not to the device in which the adsorbent is embedded in.

The adsorber can be employed for the adsorption of compounds containing oxygen and/or sulphur out of organic compositions. Preferably, the adsorber can be employed for the adsorption of ethers, alcohols, thiols, thioethers, sulfoxides, ketones, aldehydes or mixtures thereof.

Any adsorbent known to the person skilled in the art being appropriate for performing the adsorption of compounds containing oxygen and/or sulphur out of organic compositions may be applied.

Preferred adsorbents are, for example, molecular sieves with a pore diameter of 4 to 15 Å. Further, molecular sieves applicable are crystalline, natural aluminosilicates, like layer lattice silicates or synthetic molecular sieves. Furthermore, commercially available molecular sieves as sold by the Bayer AG, Dow, Union Carbide, Laporte or Mobil may be used. These molecular sieves can be, for example, zeolites of the A-, X- and Y-type. Moreover, synthetic molecular sieves comprise silicon and aluminum as main components, whereby other atoms as side-components such as lanthanides like gallium, indium and lanthanum or other elements like nickel, cobalt, copper, zinc or silver may be useful. These can be introduced into the zeolite for example by means of an ion-exchange with exchangeable cations.

Likewise, synthetic zeolites can be employed, in which other atoms like boron or phosphorus are incorporated in the layer by co-precipitation.

Further suitable adsorbents are aluminum phosphate, silicon dioxide, kieselgur, titanium dioxide, zirconium dioxide, polymeric adsorbents and mixtures thereof.

The most preferred adsorbent is aluminum oxide, commercially available for example as Selexsorb CDL from BASF.

Preferably the adsorber (A1) is based on aluminum oxide and/or the adsorber (A1) can be employed for the adsorption of compounds containing oxygen and/or sulphur out of organic compositions, preferably the adsorber (A1) can be employed for the adsorption of ethers, alcohols, thiols, thioethers, sulfoxides, ketones, aldehydes or mixtures thereof.

In step b) organic composition (OC2) is oligomerized in the presence of a catalyst, wherein at least one of the olefins of (OC2) is at least partially oligomerized, obtaining an organic composition (OC3) comprising a reduced amount of at least one olefin and an increased amount of at least one oligomerized olefin, compared to the respective amounts in (OC2).

Oligomerization, within the present invention, is defined as a catalyzed chemical reaction, in which at least two olefins are connected to an oligomerized olefin, with a higher molecular weight than each of the at least two olefins connected, over a newly formed single bond and wherein at least one double bond of the at least two olefins, per newly formed connecting single bond in the oligomerized olefin, is transformed into a single bond.

If not more than two olefins per oligomerized olefin were connected, for this reaction the term dimerization may be used.

It is not differentiated between constitutional and stereoisomers of the oligomerized olefins.

Preferably the at least one oligomerized olefin has a higher molecular weight than the at least one olefin from organic compositions originating from and/or being fed into steps preceding step b).

Preferably the at least one oligomerized olefin is octene.

Preferably at least 10 wt-%, more preferably at least 20 wt-% of the at least one olefin of (OC2) is oligomerized.

The oligomerization according to step b) may be carried out i) with a catalyst comprising 10 bis 70 wt-% NiO, 5 to 30 wt-% $TiO_2$ and/or $ZrO_2$, 0 to 20 wt-% $Al_2O_3$, 20 to 40 wt-% $SiO_2$ and 0.01 to 1 wt-% of an alkali metal oxide, preferably the catalyst comprises at least 50 wt-% NiO and 0 wt-% Al and/or ii) at a pressure of 10 to 300 bar, preferably 10 to 50 bar, most preferably at pressure of 10 to <30 bar and/or iii) at a temperature of 20 to 280° C., preferably at a temperature of 30 to 130° C. and/or iv) adiabatically, without additional measures taken for cooling by means of an heat exchange medium and/or v) in a fixed bed process.

The organic compositions (OC3) and (OC5), ((OC5) as defined below), preferably comprise octene.

Organic composition (OC3) preferably comprises at least one alkane.

Organic composition (OC3) preferably comprises at least 5 wt-% of octene.

The organic composition (OC3) preferably comprises not more than 10 wt-ppm of compounds containing oxygen and/or sulphur.

In a preferred embodiment of the invention, i) the oligomerization according to step b) is a dimerization and/or ii) the olefin in the organic composition (OC2) is butene, which is at least partially dimerized to octene.

Preferably at least 10 wt-%, more preferably at least 20 wt-%, of the butene in the organic composition (OC2) is dimerized to octene.

In a further embodiment of the invention step b) and c) are carried out more than one time during the process.

In this embodiment, the oligomerized olefins are separated from the organic composition obtained comprising the application of step c) after finishing a step according to step b). In the following step b), the corresponding organic composition obtained from the upper part of the distillation column in step c) is reused instead of (OC2). In the respective next step following the last, step b) is carried out, whereby the organic composition corresponding to (OC3) is applied.

Preferably step b), in the embodiment as specified in the preceding paragraph, is carried out at least three times.

In step c) an organic composition (OC3) is distilled in a distillation column (D1), wherein
i) an organic composition (OC4) is obtained from the upper part of (D1) and (OC4) comprises at least one alkane, at least one olefin and a reduced amount of at least one oligomerized olefin compared to the respective amount in (OC3),
ii) an organic composition (OC5) is obtained from the lower part of (D1) and (OC5) comprises at least 80% by weight, preferably at least 95% by weight of the at least one oligomerized olefin present in organic composition (OC3).

The organic composition (OC4) may comprise at least 20 wt-% alkane, preferably butane, and less than 5 wt-% oligomerized olefin, preferably octene.

Any distillation column known to the person skilled in the art being appropriate for performing the distillation in step c) and/or step f) (as defined below) may be employed.

Distillation column (D1) and/or distillation column (D2) ((D2) as defined below) may serve the purpose of removing iso-butane and the respective organic composition fed into (D1) and/or (D2) comprises butane and/or butene.

Organic composition (OC5) may comprise additionally at least one alkane.

In step d) organic composition (OC4) is hydrogenated to obtain an organic composition (OC11) comprising at least one alkane and a further reduced amount of the at least one olefin and/or of the at least one oligomerized olefin compared to organic composition (OC4).

Organic composition (OC11) comprises preferably not more than 1000 wt-ppm olefin, more preferably not more than 500 wt-ppm olefin, most preferably not more than 100 wt-ppm olefin, preferably the olefin is butene.

The hydrogenation may be carried out by any appropriate method known to the person skilled in the art.

Useful may be a catalyzed hydrogenation using at least a catalyst and a hydrogen source.

Preferably, the catalyst comprises d-block elements, more preferably, for example, Pd, Pt, Ru, Ir, Rh, Cu, Ni or Co, most preferably Pd, Ni, Pt or Rh, in particular preferably Pd or Ni.

The hydrogenation can be performed using $H_2$-gas and/or as catalytic transfer hydrogenation, employing for example ammonium formate, silyl hydrides, $NaBH_4$, cyclohexene or alcohols like methanol and propanol as hydrogen source. Preferably, the hydrogenation is carried out using $H_2$-gas as hydrogen source.

The hydrogen source and the solvent may be identical, for example, in the case of alcohols like methanol.

Any solvent known to the person skilled in the art being appropriate for performing the hydrogenation may be employed.

In general polar-protic, polar-nonprotic and/or unpolar solvents can be employed, for example methanol, ethanol, propanol, isopropanol, tetrahydrofuran or toluene.

Alternatively, the hydrogenation can be carried out without using any solvent.

In a preferred embodiment, the hydrogenation is carried out without the use of any solvent and with $H_2$-gas as hydrogen source.

Any reactor known to the person skilled in the art being appropriate for performing the hydrogenation may be employed.

Preferably a trickle bed reactor is employed for performing the hydrogenation.

In step e) an adsorber is regenerated employing organic composition (OC11) as regeneration media.

Regeneration, in the context of the present invention, means desorption and removal of adsorbed compounds containing oxygen and/or sulfur from the adsorber, in particular from the adsorbent in the adsorber. Regeneration of the adsorber may also comprise additional measures/steps necessary, for example, for preparation of the regeneration medium, the adsorber itself for regeneration or for enabling the adsorber after finished regeneration to be operated again for adsorption of compounds containing oxygen and/or sulphur out of organic compositions.

Consequently, an adsorber, within this invention, can at least be operated in the modes of operation: operation mode or regeneration mode.

An adsorber, within this invention, is in operation mode, when a stream comprising an organic composition (OC1), (OC9) or (OC10) ((OC9 and (OC10) as defined below) comprising at least one alkane and/or at least one olefin and compounds containing oxygen and/or sulfur, preferably not being routed through the adsorber before, is fed into the adsorber and compounds containing oxygen and/or sulfur are adsorbed completely or at least partially from this stream on the adsorbent.

Preferably at least 50%, more preferably at least 80%, most preferably at least 97% of the compounds containing oxygen and/or sulfur are adsorbed from the stream comprising organic composition (OC1), (OC9) or (OC10) according to the preceding paragraph.

An adsorber, within this invention, is in regeneration mode when measures to remove or measures related to the removal of adsorbed compounds containing oxygen and/or sulphur from the adsorbent are carried out or optionally the definition of the operation mode does not apply.

In a further embodiment of the invention, the at least one adsorber in step a) is an adsorber (A1) and at least one further adsorber (A2) is present in the process, and adsorber (A2) is regenerated according to step e).

Preferably the adsorbers (A1) and (A2) are operated in parallel and (A1) is in operation mode according to step a), while (A2) is in regeneration mode according to step e).

Prior to step d) an additional step f) may be carried out, comprising
f) distillation of organic composition (OC4) in a distillation column (D2), wherein
  i) an organic composition (OC2a) is obtained from the upper part of (D2) and (OC2a) comprises at least one alkane and a reduced amount of at least one olefin compared to the respective amount in (OC2), (OC3) or (OC4), with use of (OC2a) rather than (OC4) in the subsequent steps;
  ii) an organic composition (OC6) is obtained from the lower part of (D2) and (OC6) comprises at least 80% by weight, preferably at least 90% by weight of the olefins present in (OC2), (OC3) or (OC4).

Preferably, step a) is carried out prior to step b), step b) is followed by step c), step c) is followed by step f), step f) is followed by step d) and step d) is followed by step e).

Distillation column (D1) and/or distillation column (D2) may be a deisobutanizer and the respective organic composition fed into (D1) and/or (D2) comprises butane and/or butene.

Preferably distillation in step f) is carried out at temperatures at the upper part of distillation column (D2) ranging from 50 to 90° C., more preferably from 60 to 80° C. and most preferably from 65 to 75° C. and/or temperatures at the lower part of the distillation column (D2) ranging from 60 to 110° C., more preferably from 70 to 100° C. and most preferably from 80 to 90° C.

Preferably distillation in step f) is carried out at pressures ranging from 8 to 15 bar, more preferably from 9 to 13 bar and most preferably from 10 to 12 bar. The pressure drop over the entire column can be, for example, 0.1 to 0.5 bar.

Preferred columns employed as distillation column (D2) may be both packed columns and/or columns having built-in column trays (tray columns) and/or columns comprising both packing and trays, beds of packing elements in parts of the column and appropriate internals (steel plates) in other parts. Preferably the tray column comprises 40 to 150, more preferably 80 to 120 trays.

Preferably the distillation column (D2) comprises at least 5, more preferably at least 10 theoretical plates. Preferably the distillation column comprises a total number of theoretical plates from 10 to 100, more preferably from 20 to 100, most preferably from 30 to 100 and in a particular preferred embodiment 40 to 70.

In a preferred embodiment, the distillation column (D2) is divided into a stripping section and an enrichment section; preferably the stripping section comprises 25 to 40 theoretical plates and the enrichment section comprises 15 to 30 theoretical plates.

Organic composition (OC2a) comprises preferably at least 96 wt-% butane and not more than 4 wt-% butene.

Prior to step b), an additional step g) may be carried out, comprising g) feeding organic composition (OC2) into a further adsorber (SA), to further lower the amount of sulfur containing compounds in order to obtain an organic composition (OC7), wherein the amount of sulfur containing compounds is lower than in (OC2), with use of (OC7) rather than (OC2) in the subsequent steps.

Preferably step a) is followed by step g), step g) carried out prior to step b), step b) is followed by step c), step c) is followed by step f), step f) is followed by step d) and step d) is followed by step e).

Organic composition (OC7) preferably comprises not more than 40 wt-ppb of compounds containing oxygen and/or sulfur.

If (OC1) and (OC2) additionally comprise at least one diene, prior to step b), an additional step h) may be carried out, comprising h) at least partial conversion of residual dienes in organic composition (OC2), into monoolefins by selective monohydrogenation, to obtain an organic composition (OC8) wherein the amount of dienes is lower and the amount of monoolefins higher compared to the amount in (OC2), with use of (OC8) rather than (OC2) in the subsequent steps.

Preferably step a) is followed by step g), step g) is followed by step h), step h) is followed by step b), step b) is followed by step c), step c) is followed by step f), step f) is followed by step d) and step d) is followed by step e).

Preferably the monohydrogenation is carried out without additional addition of carbon monoxide.

Preferably the organic composition (OC8) comprises not more than 1 wt-% of dienes, preferably butadiene, and/or at least 20 wt-% of monoolefins, preferably butene.

Preferably at least 60 wt-%, more preferably at least 80 wt-%, most preferably at least 90 wt-% of the residual dienes are converted into monoolefins by selective monohydrogenation.

If organic composition (OC1) additionally comprises at least one halogen and/or halogen-containing compound, preferably at least one chloride and/or chlorine-containing compound, prior to step a) an additional step i) may be carried out, comprising i) feeding organic composition (OC1) into a chloride adsorber (CIA) in order to obtain an organic composition (OC9) wherein the amount of halogen, preferably of chloride and/or the amount of halogen-containing compounds, preferably of chlorine-containing compounds is lowered compared to (OC1), with use of (OC9) rather than (OC1) in the subsequent steps.

Preferably step i) is carried out prior to step a), step a) is followed by step g), step g) is followed by step h), step h) is followed by step b), step b) is followed by step c), step c) is followed by step f), step f) is followed by step d) and step d) is followed by step e).

Preferably the organic composition (OC9) comprises not more than 50 wt-ppm, more preferably not more than 10 wt-ppm, most preferably not more than 1 wt-ppm of halogen and/or halogen containing compounds, preferably chloride and/or chlorine containing compounds.

If the organic composition (OC1) additionally comprises water, prior to step a) an additional step j) may be carried out, comprising j) lowering the water content in organic composition (OC1), preferably by distillation, obtaining an organic composition (OC10), with use of (OC10) rather than (OC1) in subsequent steps.

Preferably step j) is carried out prior to step i), step i) is carried out prior to step a), step a) is followed by step g), step g) is followed by step h), step h) is followed by step b), step b) is followed by step c), step c) is followed by step f), step f) is followed by step d) and step d) is followed by step e).

Preferably the water content in the organic composition (OC10) is lower than 5 ppm, more preferably lower than 3 ppm, most preferably lower than 1 ppm.

In one further embodiment the process according to the present invention, comprises at least one, preferably all of the options i) to xv) as follows:

i) the alkane in organic composition (OC1) is butane and the olefin in (OC1) is butene, and/or ii) the organic compositions (OC1), (OC2), (OC7), (OC8), (OC9), and (OC10) comprise linear and branched alkanes, and/or olefins, and/or iii) the organic compositions (OC3) and (OC5) comprise octene, and/or iv) the organic composition (OC1) comprises at least 20 wt-% of the at least one olefin, preferably butene, and/or at least 20 wt-% of the at least one alkane, preferably butane, and/or v) the organic composition (OC3) comprises at least 5 wt-% of octene, and/or vi) the organic composition (OC1) comprises at most 1 wt % of compounds containing oxygen and/or sulfur, and/or vii) the organic composition (OC1) comprises at least 15 wt-ppm of at least one compound containing oxygen and/or sulfur, and/or viii) the organic composition (OC2) comprises not more than 10 wt-ppm of compounds containing oxygen and/or sulfur, and/or ix) the organic composition (OC3) comprises not more than 5 wt-ppm of compounds containing oxygen and/or sulfur, and/or x) the organic composition (OC8) comprises not more than 1 wt-% of dienes, preferably butadiene and/or at least 20 wt-% of monoolefins, preferably butene, and/or xi) the organic composition (OC9) comprises not more than 50 wt-ppm of halogen and/or halogen containing compounds, preferably chloride and/or chlorine containing compounds, and/or xii) the organic composition (OC4) comprises at least 20 wt-% alkane, preferably butanes, and not more than 5 wt-% oligomerized olefin, preferably octene, and/or xiii) the water content in the organic composition (OC10) is lower than 5 wt-ppm, preferably lower than 3 wt-ppm, most preferably lower than 1 wt-ppm, and/or xiv) organic composition (OC11) comprises not more than 1000 wt-ppm olefin, preferably not more than 500 wt-ppm olefin, most preferably not more than 100 wt-ppm olefin, preferably the olefin is butene, and/or xv) organic composition (OC2a) comprises at least 96 wt-% butane and not more than 4 wt-% butene.

FIGURES

FIGS. 1 to 3 illustrate certain aspects of the invention. For the sake of clarity not all applicable components and embodiments are drawn in one and/or all figures. Embodiments shown in different figures may be combined with each other and do not exclude the incorporation of further components within the limits of the disclosure of the specification.

Figure 1:
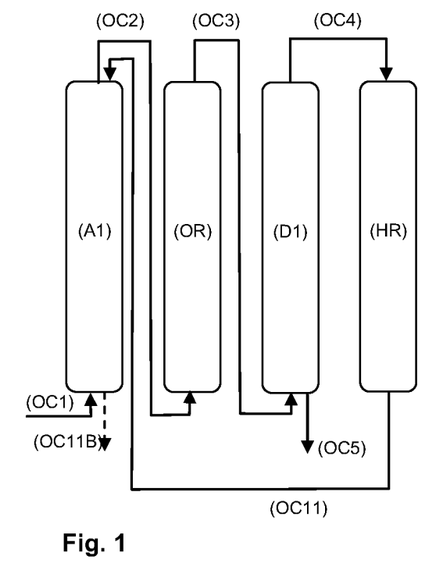

FIG. 1 illustrates the most basic assembly of the present invention. Organic composition (OC1) comprising at least one alkane and/or at least one olefin and at least one compound containing oxygen and/or sulphur is fed into adsorber (A1), run in operation mode, in order to obtain a composition (OC2) comprising at least one alkane and/or at least one olefin and a reduced amount of at least one compound containing oxygen and/or sulphur compared to the respective amount in organic composition (OC1).

The organic composition (OC2) is subsequently fed into an oligomerization reactor (OR) wherein at least one of the olefins is at least partially oligomerized, obtaining an organic composition (OC3) comprising a reduced amount of at least one olefin and an increased amount of at least one oligomerized olefin, compared to the respective amounts in (OC2).

Organic composition (OC3) is fed into distillation column (D1) and an organic composition (OC4) comprising at least one alkane, at least one olefin and a reduced amount of at least one oligomerized olefin compared to the respective amount in (OC3) is obtained from the upper part of (D1). From the lower part of (D1) an organic composition (OC5) is obtained comprising at least 80% by weight, preferably at least 95% by weight of the at least one oligomerized olefin present in organic composition (OC3).

(OC4) is subjected to a hydrogenation in a hydrogenation reactor (HR) yielding an organic composition (OC11) comprising at least one alkane and a further reduced amount of the at least one olefin and the at least one oligomerized olefin compared to organic composition (OC4).

Organic composition (OC11) is used as regeneration media in adsorber (A1) only when (A1) is operated in regeneration mode. (OC11B) leaving the adsorber during regeneration mode (dotted arrow), preferably at the opposite side of its entrance in the adsorber (A1), may comprise a higher amount of compounds containing oxygen and/or sulphur than the organic composition (OC11) fed into the adsorber.

Figure 2:
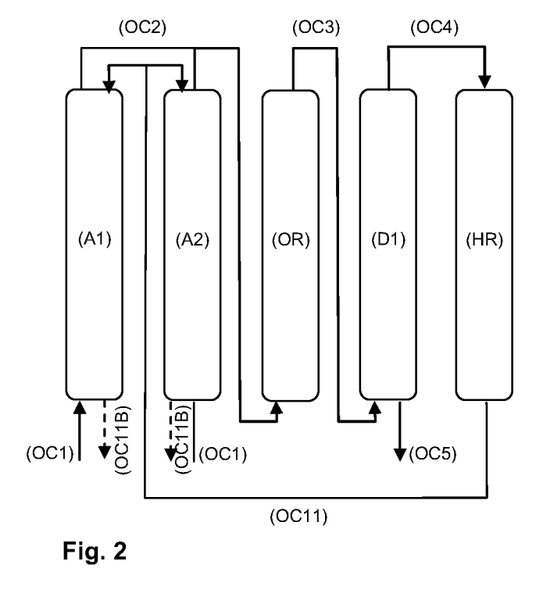

FIG. 2 shows an embodiment of the invention in which two adsorbers (A1) and (A2) are incorporated in the process operated in parallel. One adsorber may be operated in operation mode at the same time as the other adsorber is run in regeneration mode When the respective adsorber is operated in regeneration mode organic composition (OC11) is fed into the adsorber. When the adsorber is operated in operation mode, organic composition (OC1) is fed into the adsorber.

Figure 3:
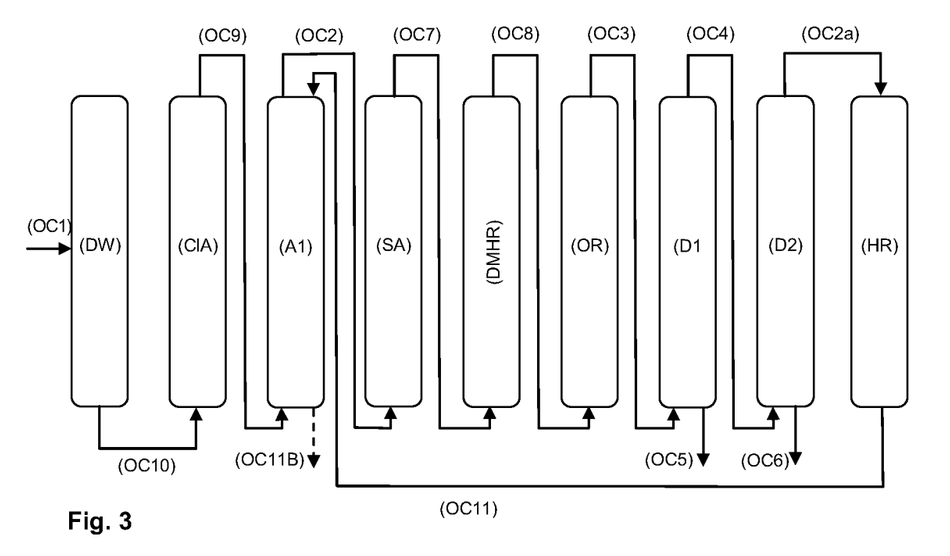

In FIG. 3 the embodiment in FIG. 1 is extended by further process steps. Before being fed into adsorber (A1) organic composition is dewatered in a dewatering unit (DW) resulting in an organic composition (OC10) with a lower water content compared to (OC1), subjected to a chlorine removal procedure in chlorine adsorber (CIA) yielding organic composition (OC9) with a lower chlorine content compared to (OC10).

(OC9) is subsequently passed through adsorber (A1).

Organic composition (OC2) is routed through a sulfur adsorber (SA) to obtain an organic composition (OC7) wherein the amount of sulfur containing compounds is lower than in (OC2).

(OC7) is fed into a diene mono-hydrogenation reactor (DMHR) in order to lower the content of dienes, resulting in an organic composition (OC8) being used in the oligomerization step in oligomerization reactor (OR).

Instead of organic composition (OC4), an organic composition (OC2a) comprising at least one alkane and a reduced amount of at least one olefin compared to the respective amount in (OC2), (OC3) or (OC4) is subjected to hydrogenation in hydrogenation reactor (HR). (OC2a) is the result of a distillation of (OC4) in a distillation column (D2) and obtained in the upper part of the column, besides an organic composition (OC6) obtained in the lower part of the column comprising at least 80% by weight, preferably at least 90% by weight of the olefins present in (OC2), (OC3) or (OC4).

The invention claimed is:

1. A process for the production of oligomerized olefins comprising the following steps a) to e):

a) purifying an organic composition (OC1) comprising at least one alkane, at least one olefin, and at least one compound containing oxygen and/or sulfur wherein the organic composition (OC1) is fed into at least one adsorber in order to obtain an organic composition (OC2) comprising at least one alkane, at least one olefin, and a reduced amount of at least one compound containing oxygen and/or sulfur compared to the respective amount in the organic composition (OC1), b) oligomerizing the organic composition (OC2) in the presence of a catalyst, wherein the at least one olefin of the organic composition (OC2) is at least partially oligomerized, to obtain an organic composition (OC3) comprising at least one oligomerized olefin and a reduced amount of the at least one olefin compared to the respective amount in the organic composition (OC2);

c) distilling the organic composition (OC3) in a distillation column (D1), wherein:
  i) an organic composition (OC4) is obtained from an upper part of (D1) and (OC4) comprises at least one alkane, at least one olefin, and a reduced amount of at least one oligomerized olefin compared to the respective amount in (OC3),
  ii) an organic composition (OC5) is obtained from a lower part of (D1) and (OC5) comprises at least 80% by weight of the at least one oligomerized olefin present in organic composition (OC3);

d) hydrogenating the organic composition (OC4) to obtain an organic composition (OC1) comprising at least one alkane and a reduced amount of the at least one olefin or a further reduced amount of the at least one oligomerized olefin compared to the respective amounts in the organic composition (OC4); and e) regenerating an adsorber (A1) employing the organic composition (OC11) as regeneration media.

2. The process according to claim 1, wherein:
   i) the oligomerization according to step b) is a dimerization; or
   ii) the at least one olefin in the organic composition (OC2) is butene, which is at least partially dimerized to octane in the oligomerization according to step b).

3. The process according to claim 1, wherein the at least one adsorber in step a) is an adsorber (A2).

4. The process according to claim 3, wherein the adsorbers (A1) and (A2) are operated in parallel and the adsorber (A2) is in operation mode according to step a), while the adsorber (A1) is in regeneration mode according to step e).

5. A process for the production of oligomerized olefins comprising the following steps a) to e):
   a) purifying an organic composition (OC1) comprising at least one alkane, at least one olefin, and at least one compound containing oxygen and/or sulfur wherein (OC1) is fed into at least one adsorber in order to obtain an organic composition (OC2) comprising at least one alkane, at least one olefin, and a reduced amount of at least one compound containing oxygen and/or sulfur compared to the respective amount in organic composition (OC1),
   b) oligomerizing the organic composition (OC2) in the presence of a catalyst, wherein the at least one olefin of the organic composition (OC2) is at least partially oligomerized, to obtain an organic composition (OC3) comprising at least one oligomerized olefin and a reduced amount of the at least one olefin compared to the respective t in the organic composition (OC2);
   c1) distilling the organic composition (OC3) in a distillation column (D1), wherein:
      i) an organic composition (OC4) is obtained from an upper part of (D1) and (OC4) comprises at least one alkane, at least one olefin, and a reduced amount of at least one oligomerized olefin compared to the respective amount in (OC3),
      ii) an organic composition (OC5) is obtained from a lower part of (D1) and (OC5) comprises at least 80% by weight of the at least one oligomerized olefin present in organic composition (OC3);
   c2) distilling the organic composition (OC4) in a distillation column (D2), wherein:
      i) an organic composition (OC2a) is obtained from an upper part of (D2) and (OC2a) comprises the at least one alkane and a reduced amount of the at least one olefin compared to the respective amount in (OC2), (OC3), or (OC4);
      ii) an organic composition (OC6) is obtained from a lower part of (D2) and (OC6) comprises at least 80% by weight of the at least one olefin present in (OC2), (OC3), or (OC4); and
   d) hydrogenating the organic composition (OC2a) to obtain an organic composition (OC11) comprising at least one alkane and a further reduced amount of the at least one olefin or of the at least one oligomerized olefin compared to the respective amounts in the organic composition (OC2a); and
   e) regenerating an adsorber (A1) employing the organic composition (OC11) as regeneration media.

6. The process according to claim 1, wherein the organic composition (OC1) comprises at least one sulfur containing compound,
   wherein the organic composition (OC2) comprises a reduced amount of the at least one sulfur containing compound compared to the amount in the organic composition (OC1), and
   wherein the process further comprises prior to step b): an additional step g), which comprises: g) feeding the organic composition (OC2) into a further adsorber (SA), to further lower the amount of the at least one sulfur containing compound in the organic composition (OC2).

7. A process for the production of oligomerized olefins comprising the following steps a) to e):
   a) purifying an organic composition (OC1) comprising at least one alkane, at least one olefin, at least one diene, and at least one compound containing oxygen and/or sulfur, wherein the organic composition (OC1) is fed into at least one adsorber in order to obtain an organic composition (OC2) comprising at least one alkane, at least one olefin, at least one diene, and a reduced amount of at least one compound containing oxygen and/or sulfur compared to the respective amount in the organic composition (OC1);
   b1) at least partially converting the at least one diene in the organic composition (OC2), into at least one monoolefin by selectively monohydrogenating the organic composition (OC2), to obtain an organic composition (OC8) comprising at least one alkane, at least one monoolefin, a reduced amount of the diene compared to the respective amount in the organic composition (OC2);
   b2) oligomerizing the organic composition (OC8) in the presence of a catalyst, wherein the at least one monoolefin of the organic composition (OC8) is at least partially oligomerized, to obtain an organic composition (OC3) comprising at least one oligomerized olefin and a reduced amount of the at least one monoolefin compared to the respective amounts in the organic composition (OC8);
   c) distilling the organic composition (OC3) in a distillation column (D1), wherein:
      i) an organic composition (OC4) is obtained from an upper part of (D1) and (OC4) comprises at least one alkane, at least one monoolefin, at least one diene, and a reduced amount of at least one oligomerized olefin compared to the respective amount in (OC3),
      ii) an organic composition (OC5) is obtained from a lower part of (D1) and (OC5) comprises at least 80% by weight of the at least one oligomenzed olefin present in organic composition (OC3);
   d) hydrogenating the organic composition (OC4) to obtain an organic composition (OC11) comprising at least one alkane and a further reduced amount of the at least one monoolefin or of the at least one oligomerized olefin compared to the respective amounts in the organic composition (OC4); and
   e) regenerating an adsorber (A1) employing the organic composition (OC11) as regeneration media.

8. The process according to claim 1, wherein the organic composition (OC1) additionally comprises at least one halogen or halogen-containing compound, and prior to step a) an additional step i) is carried out, comprising
   i) feeding organic composition (OC1) into a halide adsorber (HA), thereby reducing the amount of the halogen or the halogen-containing compound in the organic composition (OC1).

9. The process according to claim 1, wherein the organic composition (OC1) additionally comprises water and prior to step a) an additional step j) is carried out, comprising
j) lowering the water content in organic composition (OC1).

10. The process according to claim 1, wherein the organic composition (OC11) comprises butane and butene.

11. The process according to claim 1, wherein:
i) the at least one alkane in organic composition (OC1) is butane and the at least one olefin in (OC1) is butene, or
ii) the organic compositions (OC1) and (OC2) comprise linear and branched alkanes or linear and branched olefins, or
iii) the organic compositions (OC3) and (OC5) comprise octene, or
iv) the organic composition (OC1) comprises at least 20 wt-% of the at least one olefin, or at least 20 wt-% of the at least one alkane, or
v) the organic composition (OC3) comprises at least 5 wt-% of octane, or
vi) the organic composition (OC1) comprises at most 1 wt-% of compounds containing oxygen and/or sulfur, or
vii) the organic composition (OC1) comprises at least 15 wt-ppm of at least one compound containing oxygen and/or sulfur, or
viii) the organic composition (OC2) comprises not more than 10wt-ppm of compounds containing oxygen and/or sulfur, or
ix) the organic composition (OC3) comprises not more than 5 wt-ppm of compounds containing oxygen and/or sulfur, or
x) the organic composition (OC4) comprises at least 20 wt-% of the at least one alkane, and not more than 5 wt-% of the at least one oligomerized olefin, or
xi) the organic composition (OC11) comprises not more than 1000 wt-ppm olefins.

12. The process according to claim 1, wherein the oligomerization in step b) is carried out:
i) with a catalyst comprising 10 to 70wt-% NiO, 5 to 30 wt-% $TiO_2$ or $ZrO_2$, 0 to 20 wt-% $Al_2O_3$, 20 to 40 wt-% $SiO_2$ and 0.01 to 1 wt-% of an alkali metal oxide, or
ii) at a pressure of 10 to 300 bar, or
iii) at a temperature of 20 to 280° C., or
iv) adiabatically, without additional measures taken for cooling by a heat exchange medium, or
v) in a fixed bed process.

13. The process according to claim 1, wherein the organic composition (OC3) comprises iso-butane and butane or iso-butane and butane, and wherein the distillation column (D1) removes iso-butane from the organic composition (OC3).

14. The process according to claim 7, wherein the selective monohydrogenation is performed without the addition of carbon monoxide.

15. The process according to claim 1, wherein the adsorber (A1) comprises an adsorbent, wherein the adsorbent is a molecular sieve or aluminum oxide, or the adsorber (A1) is used for the adsorption of compounds containing oxygen and/or sulfur out of organic compositions.

16. The process according to claim 10, wherein the organic composition (OC11) comprises at least 96 wt-% butane and not more than 4 wt-% butene.

17. The process according to claim 11, wherein:
i) the at least one olefin in the organic composition (OC1) comprises butene or the at least one alkane in the organic composition (OC1) comprises butane, or
ii) the organic composition (OC4) comprises at least 96 wt-% butane and not more than 4 wt-% butene.

* * * * *

UNITED STATES PATENT AND TRADEMARK OFFICE
CERTIFICATE OF CORRECTION

PATENT NO. : 10,550,047 B2
APPLICATION NO. : 15/517695
DATED : February 4, 2020
INVENTOR(S) : Hans-Guenter Wagner et al.

It is certified that error appears in the above-identified patent and that said Letters Patent is hereby corrected as shown below:

In the Claims

Column 12, Line 67, Claim 1, "(OC1)" should read -- (OC11) --.

Column 13, Line 37, Claim 5, "t" should read -- amount --.

Column 14, Line 52, Claim 7, "oligomenzed" should read -- oligomerized --.

Column 15, Line 29, Claim 11, "10wt-ppm" should read -- 10 wt-ppm --.

Column 16, Line 5, Claim 12, "70wt-%" should read -- 70 wt-% --.

Column 16, Line 16, Claim 13, "iso-butane and butane," should read -- iso-butane and butene, --.

Signed and Sealed this
Fourteenth Day of July, 2020

Andrei Iancu
*Director of the United States Patent and Trademark Office*